(12) United States Patent
Mast et al.

(10) Patent No.: US 11,311,321 B2
(45) Date of Patent: Apr. 26, 2022

(54) ROTATING ROD REDUCER

(71) Applicant: Zimmer Biomet Spine, Inc., Westminster, CO (US)

(72) Inventors: Randall G. Mast, Denver, CO (US); Allison Christine Capote, Boulder, CO (US); Caleb Lee Stoll, Broomfield, CO (US)

(73) Assignee: ZIMMER BIOMET SPINE, INC., Westminster, CO (US)

( * ) Notice: Subject to any disclaimer, the term of this patent is extended or adjusted under 35 U.S.C. 154(b) by 155 days.

(21) Appl. No.: 16/588,610

(22) Filed: Sep. 30, 2019

(65) Prior Publication Data

US 2020/0100818 A1     Apr. 2, 2020

Related U.S. Application Data

(60) Provisional application No. 62/739,544, filed on Oct. 1, 2018.

(51) Int. Cl.
*A61B 17/70* (2006.01)
*A61B 17/00* (2006.01)
*A61B 17/56* (2006.01)

(52) U.S. Cl.
CPC .. *A61B 17/7086* (2013.01); *A61B 2017/0042* (2013.01); *A61B 2017/564* (2013.01)

(58) Field of Classification Search
CPC .......... A61B 17/7086; A61B 2017/291; A61B 2017/292
See application file for complete search history.

(56) References Cited

U.S. PATENT DOCUMENTS

| | | | |
|---|---|---|---|
| 5,308,357 | A | 5/1994 | Lichtman |
| 5,616,143 | A | 4/1997 | Schlapfer et al. |
| 6,261,296 | B1 | 7/2001 | Aebi et al. |
| 6,440,133 | B1 | 8/2002 | Beale et al. |
| 6,746,449 | B2 | 6/2004 | Jones et al. |
| 7,909,835 | B2 | 3/2011 | Oribe et al. |
| 8,192,438 | B2 | 6/2012 | Garamszegi |

(Continued)

OTHER PUBLICATIONS

"Canadian Application Serial No. 3,057,358, Office Action dated Jan. 18, 2021", 3 pgs.

(Continued)

*Primary Examiner* — Julianna N Harvey

(57) ABSTRACT

A rod reducer can comprise a reducing mechanism, a hinge mechanism, a handle mechanism and a bearing mechanism. The reducing mechanism can comprise a first elongate member extending along an axis to engage a bone anchor, and a second elongate member configured to slide along the first elongate member to engage a rod. The hinge mechanism can slidably couple the first and second elongate members such that the elongate members can translate against each other. The handle mechanism can comprise handles coupled to the hinge mechanism and configured to cause the first and second elongate members to translate relative to each other. The beating mechanism can be configured to permit the handles to rotate about the axis independent of the elongate members. Methods of using the rotating rod reducer can include rotating the handles out of the way of adjacent levels of a spinal column being simultaneously reduced.

17 Claims, 10 Drawing Sheets

(56) References Cited

U.S. PATENT DOCUMENTS

| | | | |
|---|---|---|---|
| RE44,296 E | 6/2013 | Beale et al. | |
| 8,636,732 B2 | 1/2014 | Davis et al. | |
| RE44,813 E | 3/2014 | Beale et al. | |
| 8,679,128 B2 | 3/2014 | Seelig | |
| 8,747,409 B2 | 6/2014 | Ichelmann et al. | |
| 2003/0009168 A1* | 1/2003 | Beale | A61B 17/7086 606/86 A |
| 2005/0261702 A1* | 11/2005 | Oribe | A61B 17/7086 606/103 |
| 2007/0282337 A1* | 12/2007 | Garamszegi | A61B 17/7086 606/53 |
| 2009/0030419 A1* | 1/2009 | Runco | A61B 17/7086 606/99 |
| 2009/0088764 A1* | 4/2009 | Stad | A61B 17/8875 606/90 |
| 2012/0078308 A1* | 3/2012 | Dziedzic | A61B 17/7086 606/264 |
| 2018/0132911 A1* | 5/2018 | Wu | A61B 17/7088 |
| 2018/0338783 A1* | 11/2018 | Mire | A61B 17/7001 |

OTHER PUBLICATIONS

"Canadian Application Serial No. 3,057,358, Response filed Mar. 10, 2021 to Office Action dated Jan. 18, 2021", 13 pgs.

"European Application Serial No. 19200898.5, Response filed Mar. 9, 2021 to Extended European Search Report dated Aug. 12, 2020", 22 pgs.

"European Application Serial No. 19200898.5, Extended European Search Report dated Aug. 12, 2020", 12 pages.

"Complaint for Patent Infringement", *SDGI Holdings, Inc. and Medtronic Sofamor Danek, Inc.* v. *EBI, L.P. and Biomet Inc.*, United States District Court District of New Jersey, Civil Action No. 2:06-cv-00490-SRC-MAS, (Feb. 1, 2006), 9 pgs.

"Vitality® Spinal Fixation System", Surgical Technique Guide—Zimmer Biomet, [Online]. [Accessed Jul. 23, 2019]. Retrieved from the Internet: <URL: https://www.zimmerbiomet.com/content/dam/zimmer-biomet-OUS-Surg-techniques/spine/vitality-spinal-fixation-system-surgical-technique.pdf>, (Mar. 2018), 60 pgs.

\* cited by examiner

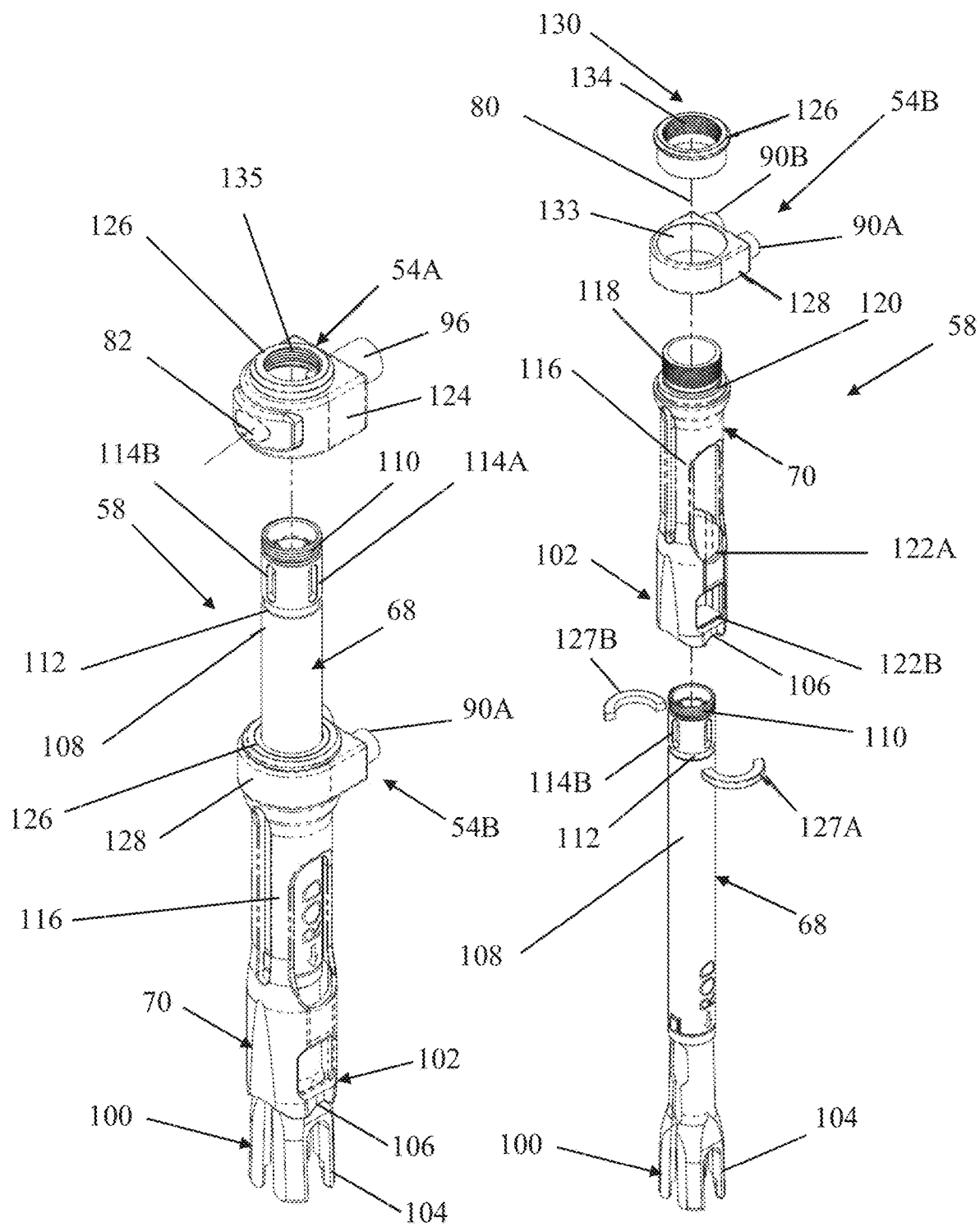
FIG. 10                    FIG. 11

ROTATING ROD REDUCER

CLAIM OF PRIORITY

This application claims the benefit of U.S. Provisional Patent Application Ser. No. 62/739,544, filed on Oct. 1, 2018, the benefit of priority of which is claimed hereby, and which is incorporated by reference herein in its entirety.

TECHNICAL FIELD

This document pertains generally, but not by way of limitation, to instruments and methods for surgical procedures, such as can be used in spinal procedures. More specifically, but not by way of limitation, the present application relates to rod reducing devices.

BACKGROUND

A spinal column can require correction of spinal deformities and abnormalities resulting from trauma or degenerative issues. Various methods of correcting issues with the spinal column can include fusing adjacent vertebrae together or immobilizing the spinal column with a rod system. For example, fasteners or other fixation devices can be attached to multiple vertebra, with each fastener serving as an anchor point for attaching the rod. The fasteners can be inserted into the vertebrae at a pedicle area of the bone such that the rod can be positioned between the spinous process and the transverse process. Rods can be placed on either side of the spinal column and can span several vertebrae. Sometimes it can be advantageous to utilize instruments to facilitate assembly of the rod with the fastener.

Examples of surgical instrumentation devices are described in U.S. Pat. No. RE44,296 to Beale et al.; U.S. Pat. No. 8,747,409 to Ichelmann et al.; U.S. Pat. No. 8,679,128 to Seelig; U.S. Pat. No. 8,192,438 to Garamszegi; and U.S. Pat. No. 7,909,835 to Oribe et al.

OVERVIEW

The present inventors have recognized, among other things, that a problem to be solved can include the inability of surgeons to reposition rod reducers once attached to a bone anchor and/or rod. Specifically, the present inventor(s) have recognized that some rod reducers having actuation handles that are fixed in an operating plane relative to the axis of reduction cannot be readily used, if at all, adjacent another bone anchor having a rod reducer attached thereto. As such, it is difficult or impractical to reduce multiple adjacent vertebra levels simultaneously, such as can be advantageous in spinal deformity applications.

The present subject matter can help provide a solution to this problem, such as by providing a rod reducer that can be actuated in multiple positions relative to the direction of reduction. In particular, a rod reducer can include actuation handles that can be actuated in any vertical plane extending parallel to the rod reduction axis to provide rod-reducing action. Furthermore, the rod-reducing actuation handles can be angled relative to the rod reduction axis to provide additional clearance between adjacent rod reducers and to provide ergonomic and mechanical benefits to the operator.

In an example, a rod reducer can comprise a first elongate member, a second elongate member configured to slide along the first elongate member, a first bearing component rotatably connected to the first elongate member, a second bearing component rotatably connected to the second elongate member, a hinge mechanism and first and second handles. The hinge mechanism can comprise a first pair of linkages pivotably coupled to the first bearing component, a second pair of linkages pivotably coupled to the second bearing component, first and second rotation elements connecting the first pair of linkages and the second pair of linkages, and first and second lever arms extending from the second pair of linkages. The first and second handles can be connected to the first and second lever arms, respectively, and can be configured to cause the second pair of linkages to draw the first bearing component and the first elongate member toward the second beating component. The first bearing component and the second bearing component can permit the hinge mechanism to rotate about the first and second elongate members.

In another example, a rod reducer can comprise a reducing mechanism, a hinge mechanism, a handle mechanism and a bearing mechanism. The reducing mechanism can comprise a first elongate member extending along an axis and configured to engage a bone anchor, and a second elongate member configured to slide along the first elongate member along the axis and configured to engage a rod. The hinge mechanism can slidably couple the first elongate member and the second elongate member such that the first elongate member can translate relative to the second elongate member. The handle mechanism can comprise a pair of handles coupled to the hinge mechanism and configured to cause the first and second elongate members to translate relative to each other. The bearing mechanism can be configured to permit the handle mechanism to rotate about the axis independent of the first and second elongate members.

In an additional example, a method of reducing multiple levels of a spinal column in a surgical procedure to correct a spinal deformity can comprise implanting a first bone anchor to a first vertebra, the first bone anchor including a first housing having a first opening to receive a rod, implanting a second bone anchor to a second vertebra, the second bone anchor including a second housing having a second opening to receive the rod, implanting a third bone anchor to a third vertebra, the third bone anchor including a third housing having a third opening to receive the rod, positioning the rod in the first opening, securing the rod to the first housing, positioning the rod proximate the second opening and the third opening, coupling a first rotating rod reducer to the second housing, reducing the rod into the second housing using the first rotating rod reducer, rotating a first pair of handles of the first rotating rod reducer away from the third bone anchor, such as into a transverse plane of the spinal column, reducing the rod into the third housing using an additional rod reducer and securing the rod to the second and third housings. The first rotating rod reducer can comprise first and second reducing elements that are configured to slide relative to each other, and the first pair of a handles configured to slide the first and second reducing elements relative to each other when actuated. The first pair of handles can be configured to rotate about an axis of the first and second reducing elements.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIG. 10 is a partially exploded perspective view of the reducing mechanism of FIGS. 4 and 5 showing upper and lower bearing components.

FIG. 11 is an exploded perspective view of the reducing mechanism of FIG. 10 with the upper bearing component removed.

Figure 1:
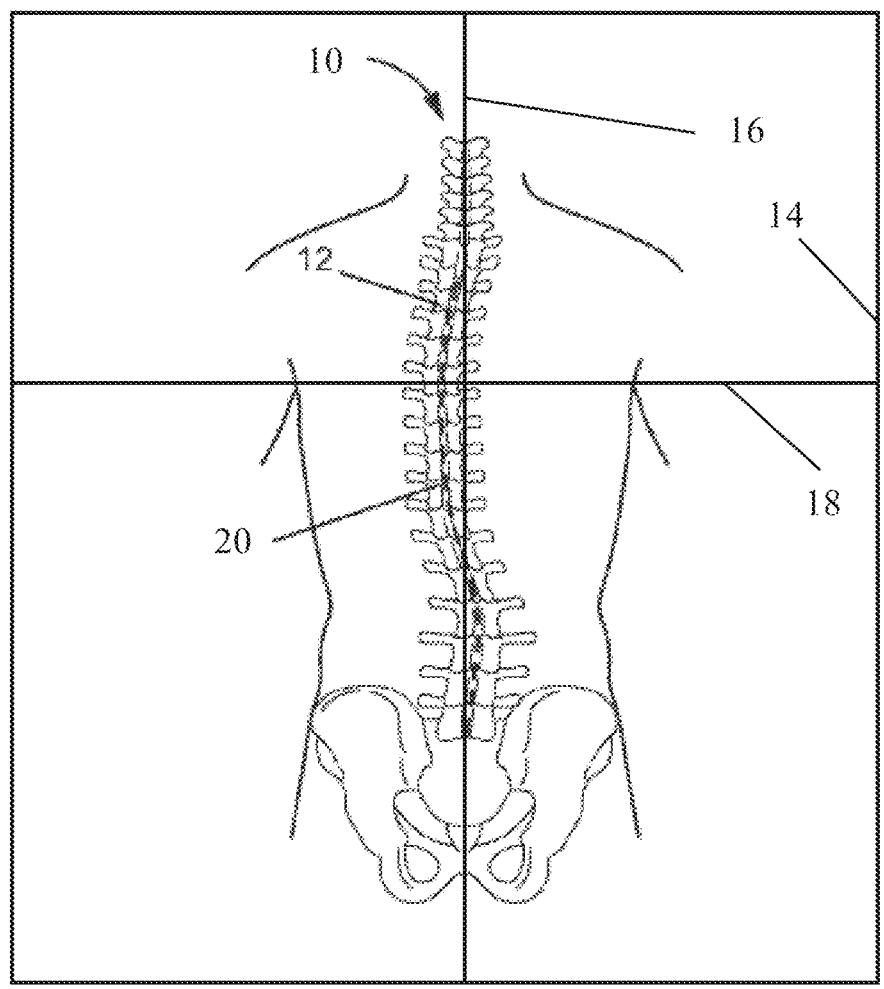
FIG. 1 is a diagrammatic view of a spinal column having a curvature deformity.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1 is a diagrammatic view of patient 10 having spinal column 12 with a curvature deformity. As viewed from the back in FIG. 1, a spinal column can have an ideal shape that is generally straight in coronal plane 14 along sagittal plane 16. However, spine 12 of patient 10 does not follow a generally straight line in coronal plane 14. Patients can have curvatures or offsets from the ideal spinal shape in coronal plane 14, sagittal plane 16 or transverse plane 18. Spine 12 of patient 10 in FIG. 1 exhibits double curve 20 in coronal plane 14, which can be consistent with scoliosis.

Figure 2:
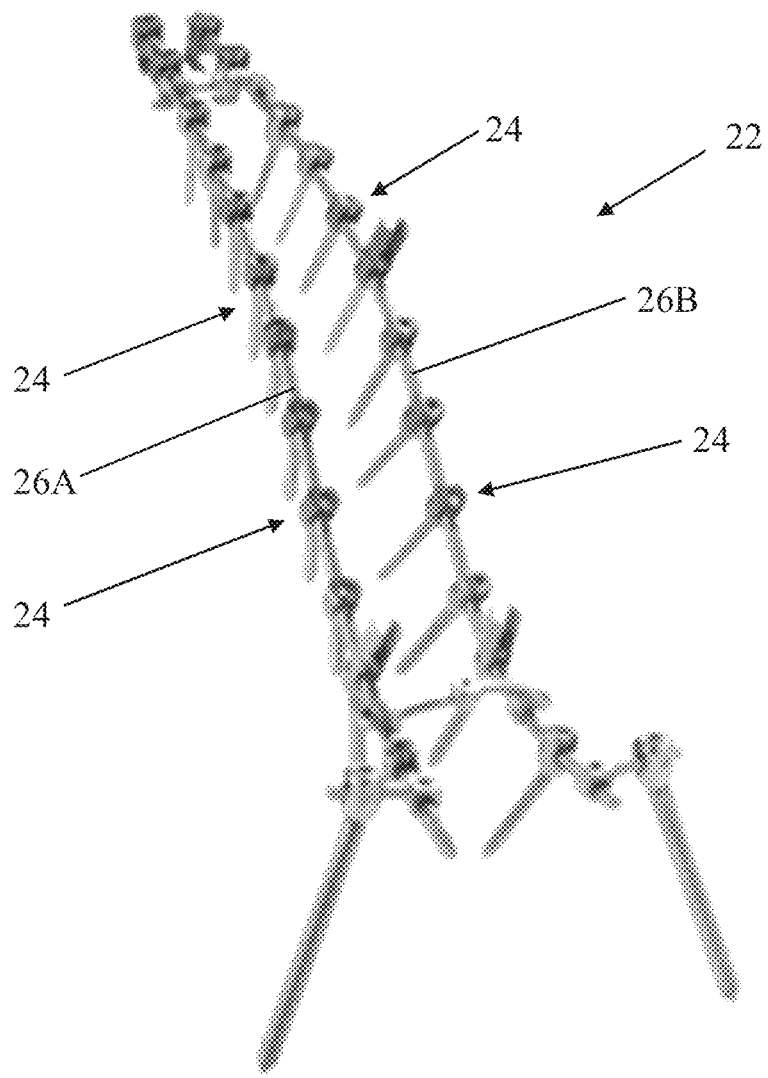
FIG. 2 is a perspective view of a spinal stabilization system including a plurality of bone anchors connected to a pair of elongate rods that can be used to correct a curvature deformity.

FIG. 2 is a perspective view of spinal stabilization system 22 including a plurality of bone anchors 24 connected to elongate rods 26A and 26B. Bone anchors 24 can be threaded into the pedicle areas of vertebrae to provide anchoring points for spinal stabilization system 22 and attachment points for rods 26A and 26B. Each bone anchors 24 can include a threaded shaft portion having a head to which a rod housing is attached, as is known in the art. One of rods 26A and 26B can be inserted into the housing and secured with a fastener. As such, with a plurality of bone anchors 24 extending along the medial and lateral sides of a spinal column, rods 26A and 26B can be secured in place to stabilize and straighten the spinal column. For example, a surgeon can bend or otherwise manipulate rods 26A and 26B before or after coupling to anchors 24 to correct a spinal deformity.

In some instances, the location of a bone anchor 24 might be such that the rod cannot be positioned within the rod housing do to movement of the rod being restricted, such as by coupling to other bone anchors 24. With reference to FIG. 1, if rod 26B were attached to bone anchors 24 attached to the right-hand side of spinal column 12 above and below transverse plane 18, it might be difficult to position rod 26B into a bone anchor 24 attached to the right-hand side of spinal column 12 attached near transverse plane 18. In such scenarios, the vertebra near transverse plane 18 might need to be reduced to pull the bone anchor up to rod 26B.

Figures 3A, 3B:
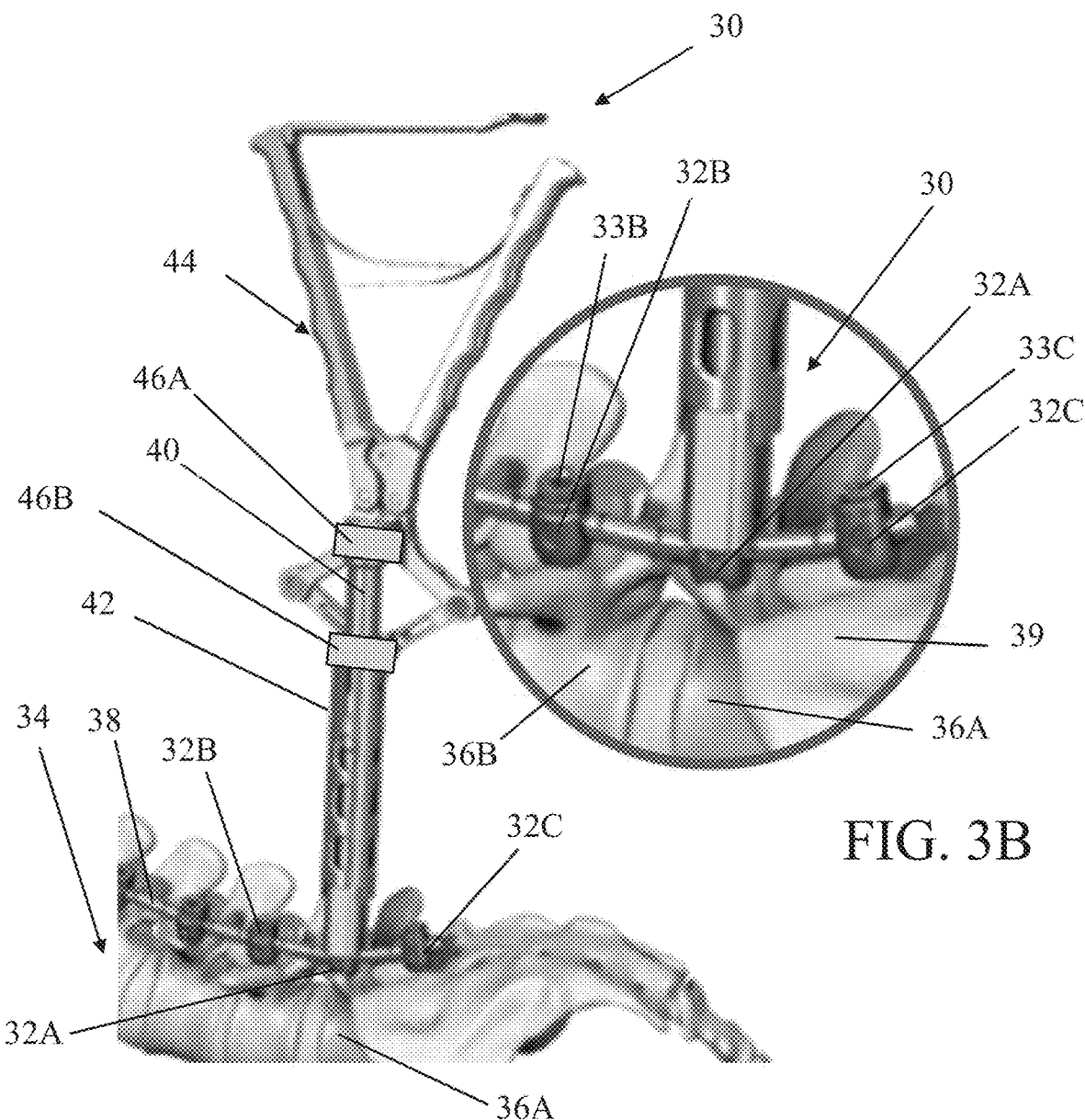
FIG. 3A is a perspective view of a rod reducer coupled to a bone anchor attached to a vertebra of a spinal column.
FIG. 3B is a close-up view of FIG. 3A showing an attachment between the rod reducer and the bone anchor.

FIG. 3A is a perspective view of rod reducer 30 coupled to bone anchor 32A, which can be attached to spinal column 34 at vertebra 36A. FIG. 3B is a close-up view of a portion of FIG. 3A showing an attachment between rod reducer 30 and bone anchor 32A. Rod 38 can be positioned within housing of bone anchors 32B and 32C and secured with fasteners 33B and 33C, respectively. Bone anchor 32B can be attached to vertebra 36B and bone anchor 32C can be attached to sacrum 39. With rod 38 fully seated in bone anchors 32B and 32C, rod 38 might not be able to seat fully within bone anchor 32A. As such, rod reducer 30 can be coupled to bone anchor 32A to pull bone anchor 32A up and around rod 38. Rod reducer 30 can include inner member 40 and outer member 42. Outer member 42 can attach to the housing of bone anchor 32A and inner member can sit atop rod 38. Handle mechanism 44 can be actuated to pull outer member 42 and bone anchor 32 upward (with reference to the orientation of FIG. 3A) to position the housing around rod 38, thereby enabling a fastener (not shown), similar to fasteners 33B and 33C, to secure rod 38 to the housing of bone anchor 32A. As such, vertebra 34A can be reduced to move toward rod 38.

With the disclosure of the present application, swivel bearings 46A and 46B can be attached to inner member 40 and outer member 42, respectively, to permit handle mechanism 44 to rotate about the actuation axis of inner member 40 and outer member 42. As such, a surgeon can reposition handle mechanism 44 for comfort, ease or mechanical advantage during a procedure. Furthermore, multiple adjacent or nearby vertebral levels of spinal column 34 can be reduced at the same time, such as can be desirable in spinal deformity applications, by positioning handle mechanism 44 to operate in a transverse plane rather than a sagittal plane as depicted in FIG. 3A.

Figure 4:
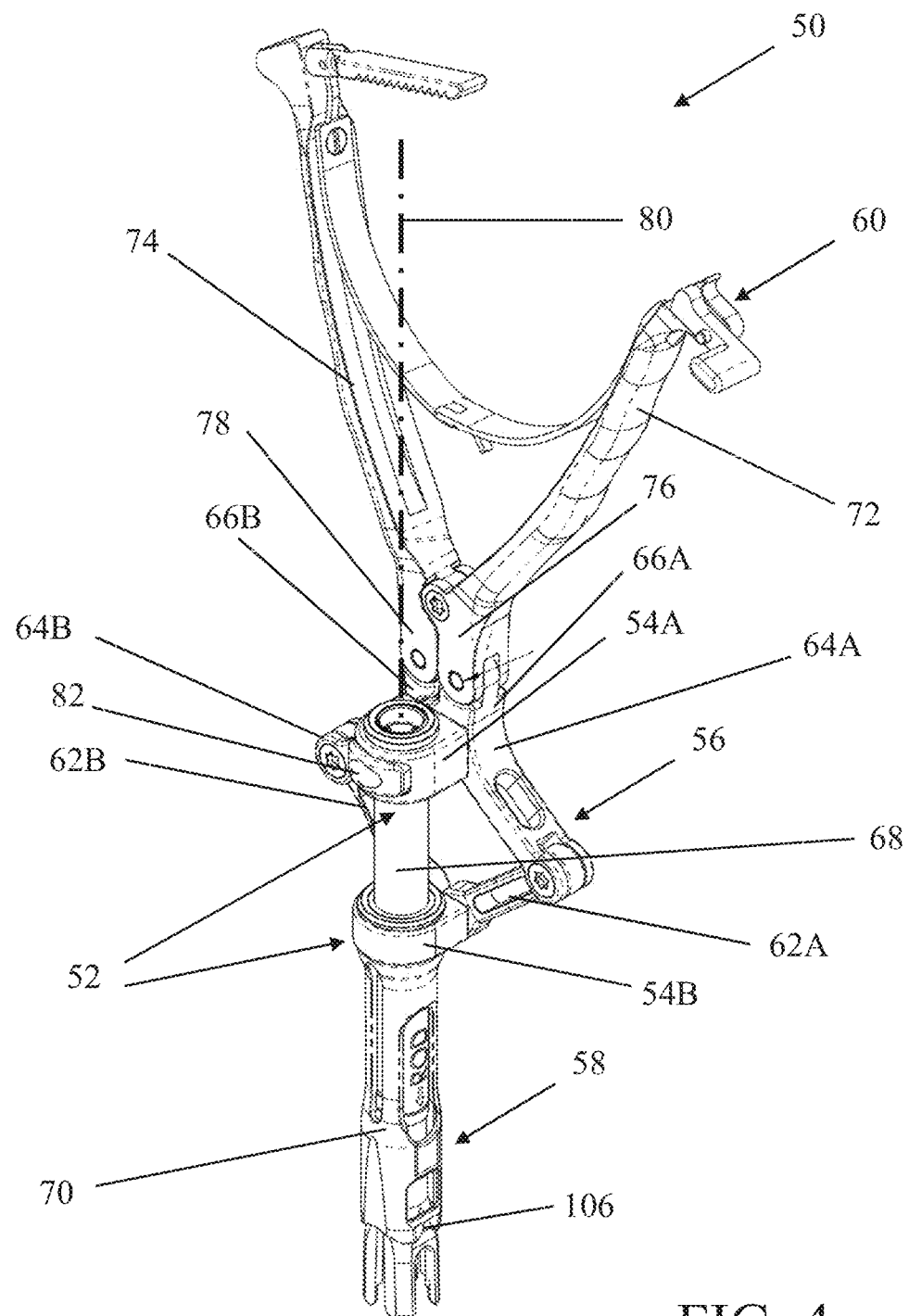
FIG. 4 is a perspective view of a rotating rod reducer of the present application including a bearing mechanism.

FIG. 4 is a perspective view of rotating rod reducer 50 of the present application including bearing mechanism 52 comprising first bearing 54A and second bearing 54B. Rotating rod reducer 50 can also comprise hinge mechanism 56, reducing mechanism 58 and handle mechanism 60. Bearing mechanism 52 can form part of hinge mechanism 58. Hinge mechanism 58 can comprise first linkages 62A and 64A, second linkages 62B and 64B, and lever arms 66A and 66B. Reducing mechanism 58 can comprise inner elongate member 68 and outer elongate member 70. Handle mechanism 60 can comprise first handle 72, second handle 74, first cam 76 and second cam 78.

Inner elongate member 68 can be positioned around an elongate stabilizing element, such as a rod, and attached to a housing of a bone anchor such that outer elongate member 70 can be positioned atop the elongate stabilizing element. With handles 72 and 74 in the depicted open position, handles 72 and 74 can be pushed together by an operator to spread apart first cam 76 and second cam 78, which can thereby push lever arms 66A and 66B apart. Such action can cause second linkages 64A and 64B to be pushed together, which can also cause first linkages 62A and 62B to be pushed together. Operation of hinge mechanism 58 in such a manner can cause outer elongate member 70 to be pulled upward via second bearing 54B and inner elongate member 68 to be pushed downward via first bearing 54A. As such, a rod positioned under outer elongate member 70 can be moved into a housing connected to inner elongate member 68. Handles 72 and 74, as well as cams 76 and 78, can be rotated around center axis 80 of inner elongate member 68 and outer elongate member 70 with bearings 54A and 54B. Bearings 54A and 54B can be configured to permit complete and continuous three-hundred-sixty-degree rotation about axis 80 or can be configured to limit rotation to a smaller range. Additionally, bearings 54A and 54B can be configured to lock the position of handles 72 and 74 relative to elongate members 68 and 70 thereby inhibiting rotation at bearings 54A and 54B. For example, button 82 can be used to control and lock rotation of handle mechanism 60.

Figure 5:
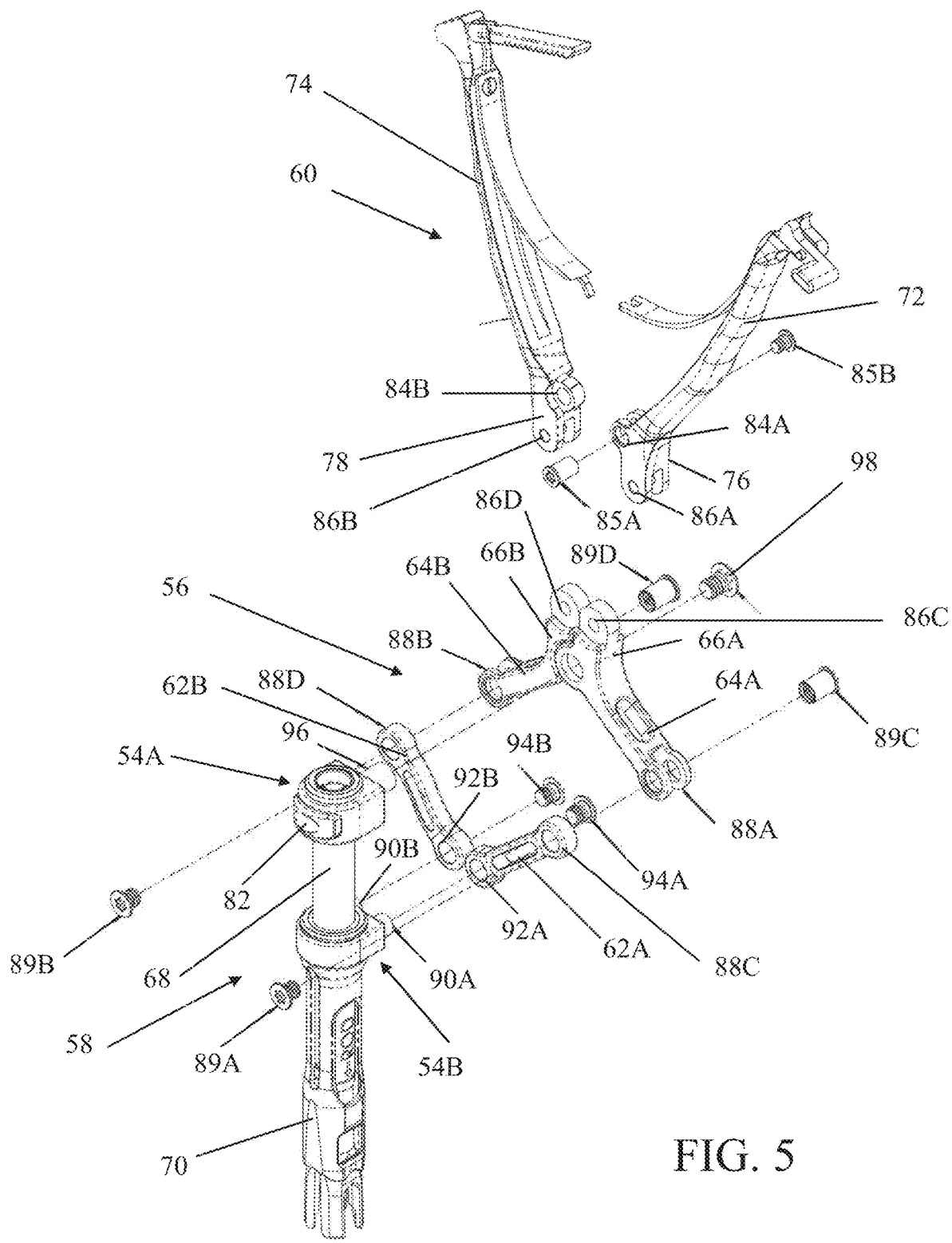
FIG. 5 is a partially exploded perspective view of the rotating rod reducer of FIG. 4 showing a hinge mechanism connecting a reducing mechanism and a handle mechanism.

FIG. 5 is a partially exploded perspective view of rotating rod reducer 50 of FIG. 4 showing hinge mechanism 56 connecting reducing mechanism 58 and handle mechanism 60.

Figures 6, 7:
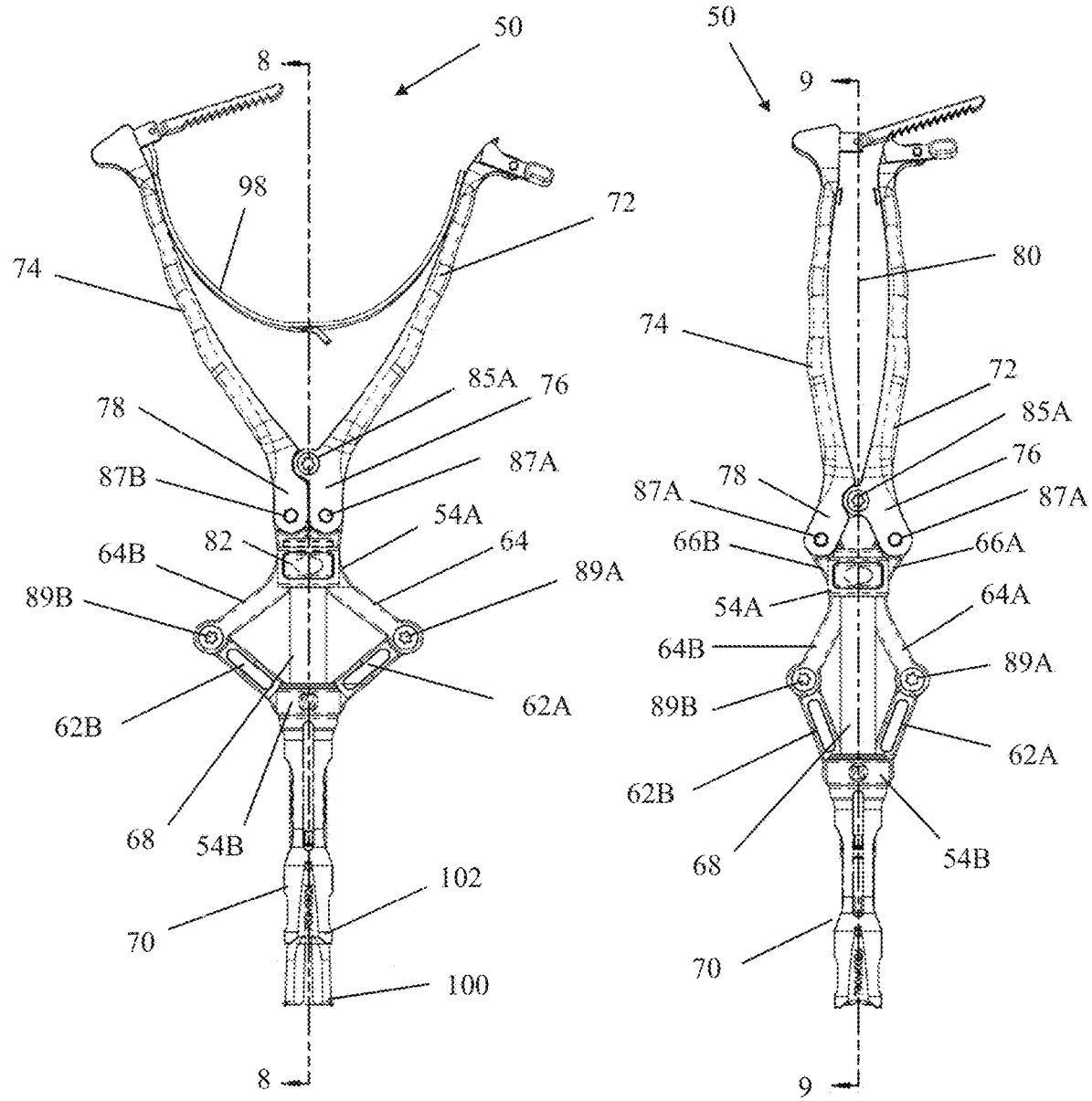
FIG. 6 is a front view of the rotating rod reducer of FIG. 4 showing rod-engaging and anchor-engaging components in an open or non-reduced state.
FIG. 7 is a front view of the rotating rod reducer of FIG. 6 showing the rod-engaging and anchor-engaging components in a closed or reduced state.

Handles 72 and 74 and cams 76 and 78 can be connected at sockets 84A and 84B that together form a pivot point for receiving fasteners 85A and 85B. Fastener 85B can be threaded into as socket within fastener 85A to, for example, prevent fasteners 85A and 85B from dislodging from reducer 50. Cams 76 and 78 can be connected to lever arms 66A and 66B at sockets 86A, 86B, 86C and 86D, respectively, to form a pivot point for receiving fasteners 87A and 87B (FIG. 6). Fasteners 87A and 87B can comprise pins force fit into sockets 86A-86D. Lever arms 66A and 66B can be connected directly to second linkages 64A and 64B. Second linkages 64A and 64B can be connected to first linkages 62A and 62B at pivot points 88A, 88B, 88C and 88D, respectively, to form a pivot point for receiving fasteners 89A, 89B, 89C and 89D. Fastener 89A can be threaded into as socket within fastener 89C, and fastener 89B can be threaded into a socket within fastener 89D to, for example, prevent fasteners 89A-89D from dislodging from reducer 50. First linkages 62A and 62B can be connected to outer elongate member 70, via bearing 54A, at pivot points formed by the coupling of posts 90A and 90B and sockets 92A and 92B, respectively, using fasteners 94A and 94B. Second linkages 64A and 64B can be connected to inner elongate member 68, via bearing 54B, at post 96. Fasteners 85A, 85B, 87A, 87B, 89A-89D, 94A, 94B, and 98 can provide rotation elements that can permit the various linkages, handles and connecting components described herein to rotate relative to each other.

FIG. 6 is a front view of rotating rod reducer 50 of FIG. 4 in an open or non-reduced state. Handles 72 and 74 can be pushed apart by spring 98 to bias reducer 50 to an open position Pushed apart, handles 27 and 74 can be rotated at fastener 85A so that cams 76 and 78 are pushed together. Cams 76 and 78 can draw lever arms 66A and 66B together via fasteners 87A and 87B. Pushed together, lever arms 66A and 66B can be rotated at post 96 (FIG. 5) to push linkages 64A and 64B apart. Pushed apart, linkages 64A and 64B can also push apart linkages 62A and 62B at fasteners 89A and 89B. Pushed apart, linkages 62A and 62B can be rotated at posts 90A and 90B (FIG. 5) to actuate outer elongate member 70. As such, when handles 72 and 74 are pushed apart, first bearing 54A can be located a first distance away from second bearing 54B. Handles 72 and 74 can be rotated at fastener 85B to change the distance between bearings 54A and 54B, as shown in FIG. 7. Although FIGS. 6 and 7 are described with reference to handles 72 and 74 that pivot at fastener 85B above elongate members 68 and 70, other handle mechanisms can be used, such as sliding handles positioned off to the side of elongate members 68 and 70.

FIG. 7 is a front view of rotating rod reducer 50 of FIG. 6 in a closed or reduced state. Handles 72 and 74 can be pushed together by an operator to overcome the force of spring 98 (not visible in FIG. 7), thereby rotating cams 76 and 78 outward at fastener 85A. Spring 98 can become tucked into cavities within handles 72 and 74. Cams 76 and 78 can cause lever arms 66A and 66B to also be rotated outward at post 96, which can cause linkages 64A and 64B to be rotated inward. Linkages 64A and 64B can push linkages 62A and 62B inward via fasteners 89A and 89B thereby causing second bearing 54B to be pushed away from first bearing 54A and outer elongate member 70 to be pushed along inner elongate member 68. As such, when handles 72 and 74 are pushed together, first bearing 54A can be located a second distance away from second bearing 54B that is greater than the first distance to provide the reducing action.

The first and second distances can also correspond to the relative locations of inner elongate member 68 and outer elongate member 70. Inner elongate member 68 can include housing-engaging feature 100 and outer elongate member 70 can include rod-engaging feature 102. Housing-engaging feature 100 can comprise a mechanism for attaching to a housing of a bone anchor. For example, housing-engaging feature 100 can comprise a plurality of tabs or fingers that can attach to the outside of the housing. The fingers can be flexible to facilitate engagement with notches or ledges on the housing that can prevent displacement of inner elongate member 68 with the housing. Housing-engaging feature 100 can comprise other suitable means for attaching to the housing, such as a threaded engagement. Housing-engaging feature 100 can include cut-outs 104 (FIGS. 8 and 9) that can permit a rod to be located in the bone anchor housing while housing-engaging feature 100 is engaged with the housing. Rod-engaging feature 102 can comprise notch 106 (FIGS. 4 and 10) at the distal end of outer elongate member 70 to facilitate seating of outer elongate member 70 on the rod. Thus, as handles 72 and 74 are moved to translate outer elongate member 70 along inner elongate member 68, housing-engaging feature 100 can be translated relative to rod-engaging feature 102 to reduce the rod and the housing relative to each other.

Figures 8, 9:
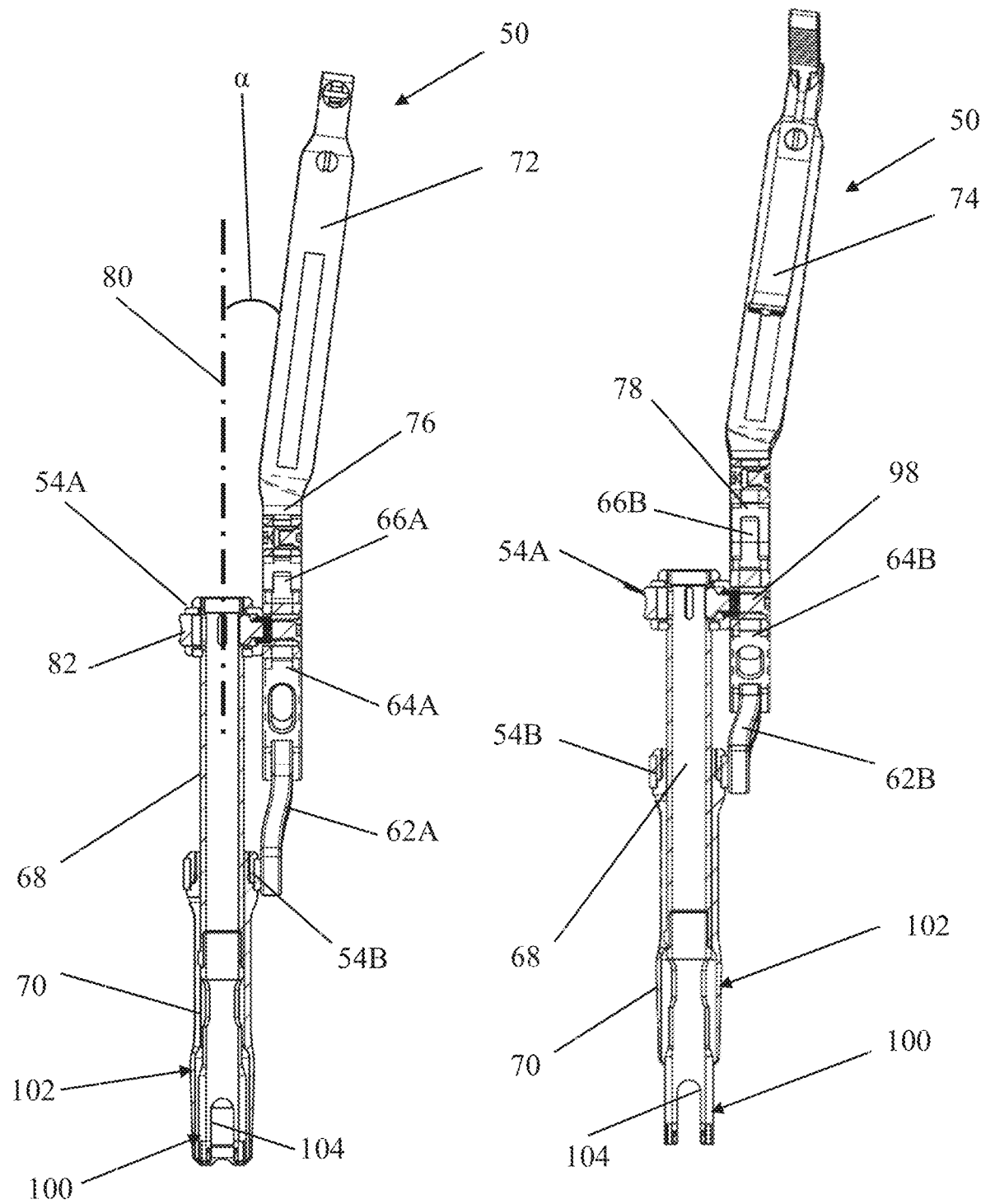
FIG. 8 is a side cross-sectional view of the rotating rod reducer of FIG. 6 taken at section 8-8 showing the rotating rod reducer in an open or non-reduced state.
FIG. 9 is a side cross-sectional view of the rotating rod reducer of FIG. 7 taken at section 9-9 showing the rotating rod reducer in a closed or reduced state.

FIG. 8 is a side cross-sectional view of rotating rod reducer 50 of FIG. 6 in an open or non-reduced state taken at section 8-8. FIG. 9 is a side cross-sectional view of rotating rod reducer 50 of FIG. 7 in a closed or reduced state taken at section 9-9. As can be seen in FIG. 8, with handles 72 and 74 pushed away from each other, rod-engaging feature 102 can be located above, or proximally of, housing-engaging feature 100. As such, rotating rod reducer 50 can be coupled to a bone anchor and a rod spaced apart from the bone anchor. As can be seen in FIG. 9, with handles 72 and 74 pushed toward each other, rod-engaging feature 102 can be located alongside, or level with, housing-engaging feature 100. As such, a bone anchor engaged with housing-engaging feature 100 can be pulled upward to engage a rod seated against rod-engaging feature 102.

As shown in FIG. 9, handle 72 can be disposed at angle α relative to axis 80 of elongate members 68 and 70. Angling of handles 72 and 74 can facilitate rotation and positioning of handles 72 and 74, as described below, to not interfere with other vertebral levels being reduced, particularly those that are immediately adjacent rod reducer 50. In an example, angle α can be approximately 15°, but can be in the range of approximately 10° to approximately 25° to provide ergonomic benefit while still being capable of providing adequate mechanical leverage.

FIGS. 8 and 9 additionally show a low-profile construction of rod reducer 50. Cams 76 and 78, lever arms 66A and 66B, linkages 64A and 64B, and linkages 62A and 62B can be located in a single plane offset from and parallel to axis 80. As such, the thickness of rod reducer 50 can be reduced in order to provide additional space alongside elongate members 68 and 70, which can provide additional clearance for adjacent instruments, such as additional rod reducers, and additional visibility for a surgeon. In order to facilitate such a construction, posts 90A and 90B can be located side-by-side at the same longitudinal level.

FIG. 10 is a partially exploded perspective view of reducing mechanism 58 of FIGS. 4 and 5 showing upper bearing 54A and lower bearing 54B. FIG. 11 is an exploded perspective view of reducing mechanism 58 of FIG. 10 with upper bearing component 54A removed. FIGS. 10 and 11 are discussed concurrently.

Figure 13:
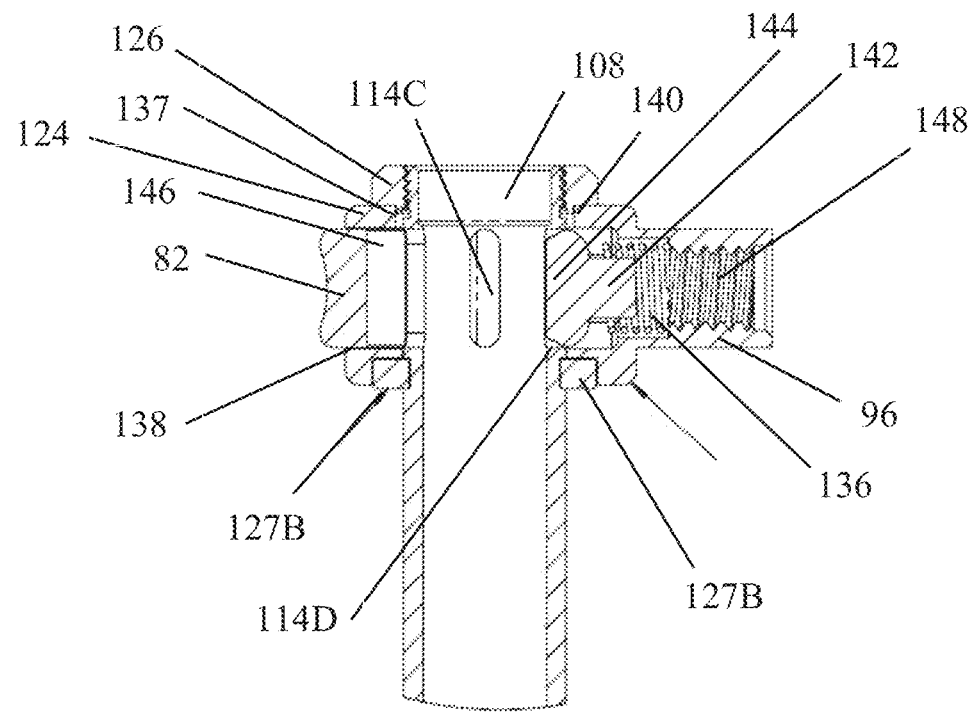
FIG. 13 is a cross-sectional view of the upper bearing component of FIG. 10 attached to an elongate reducing member.

Inner elongate member 68 can comprise tubular body 108, housing-engaging feature 100 located at a first, distal end of tubular body 108, threading 110 located at a second, proximal end of tubular body 108, groove 112, first detent 114A, second detent 114B, third detent 114C (FIG. 13) and fourth detent 114D (FIG. 13). Outer elongate member 70 can comprise tubular body 116, rod-engaging feature 102 located at a first, distal end of tubular body 116, threading 118 located at a second, proximal end of tubular body 116, shelf 120 and windows 122A and 122B.

Bodies 108 and 116 can be tubular to facilitate insertion of a driver device, e.g., a screw driver, through reducing mechanism 58 to couple a closure member, e.g., a threaded fastener, to a housing of a bone anchor. Body 116 can include windows 122A and 122B to permit body 108 and cut-outs 104 to be viewed with retracted into body 116.

Upper bearing 54A can comprise bearing housing 124, button 82, bushing 126, post 96, and lock ring components 127A and 127B. Lower bearing 54B can comprise bearing housing 128, posts 90A and 90B and bushing 130.

Bearing housing 128 of lower bearing 54B can be positioned around tubular body 116 to rest on shoulder 120. Bushing 130 can be inserted into longitudinal passage 133 of bearing housing 128 so as to be radially between bearing housing 128 and threading 118 relative to axis 80. Internal threading 134 of bushing 130 can be engaged with threading 118 of tubular body 116, thereby axially trapping bearing housing 128 between a flange on bushing 130 and shoulder 120. However, bearing housing 128 can still be disposed to circumferentially rotate about axis 80.

Bearing housing 124 of upper bearing 54A can coupled to the first, proximal end of tubular body 108. Lock ring components 127A and 127B can be positioned into groove 112 and bearing housing 124 can be positioned to retain lock ring components 127A and 127B within groove 112. Bushing 126 can be inserted into longitudinal passage 137 (FIG. 12) of bearing housing 124 so as to be radially between bearing housing 124 and threading 110 relative to axis 80. Internal threading 135 of bushing 126 can be engaged with threading 110 of tubular body 108, thereby axially trapping bearing housing 124 between a flange on bushing 130 and locking ring components 127A and 127B. However, bearing housing 124 can still be disposed to circumferentially rotate about axis 80.

Although aspects of the present disclosure are described with reference to bearings 54A and 54B comprising bushing elements, other types of devices to facilitate rotation of handle mechanism 60 and hinge mechanism 56 can be used. For example, roller bearings or ball bearings can be used. Additionally, in other embodiments, bearings 54A and 54B can be configured to operate without bushings 1226 and 130 such that housings 124 and 128 can directly rotate against elongate members 68 and 70, respectively.

Figure 12:
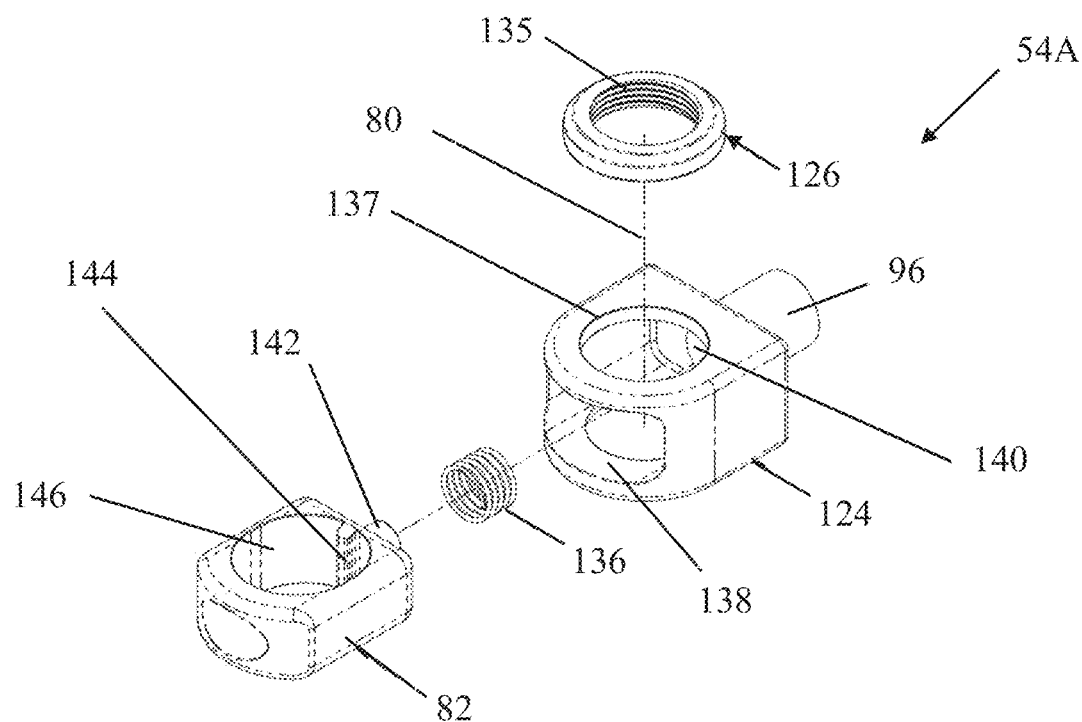
FIG. 12 is an exploded perspective view of the upper bearing component of FIG. 10.

FIG. 12 is an exploded perspective view of upper bearing 54A of FIG. 10. FIG. 13 is a cross-sectional view of upper bearing 54A of FIG. 10. FIGS. 12 and 13 are discussed concurrently. As shown in FIG. 12, upper bearing 54A can further comprise spring 136, bearing housing 124 can further comprise longitudinal passage 137, transverse passage 138 and spring socket 140, and button 82 can further comprise spring post 142, lock prong 144 and longitudinal passage 146. Post 96 can comprise fastener port 148.

Spring 136 can be positioned around spring post 142. Button 82 can be inserted into transverse passage 138 of bearing housing 124 such that longitudinal passage 146 generally aligns with longitudinal passage 137. Spring 136 and spring post 142 can thereby be inserted into spring socket 140 within post 96. Lock ring components 127A and 127B can be positioned into channel 112. Longitudinal passage 146 of button 82 can be positioned around tubular body 108 to hold lock ring components 127A and 127B into place. Longitudinal passage 137 of housing 124 can have a slightly larger diameter than the outer diameter of tubular member 108 so that housing 124 cannot be radially displaced relative to axis 80. Longitudinal passage 146 of button 82 can be wider than longitudinal passage 137 of housing 124 in order to permit button 82 to be radially displaced within transverse passage 138 alongside tubular member 108 to engage and disengage lock prong 144 with detents 114A-114D.

Spring 136 can bias button 82 out of transverse passage 138 such as by pushing against spring socket 140 and button 82. Tubular member 108 can prevent button 82 from being dislodged from transverse passage 138. Button 82 can be pushed further into transverse passage 138 to overcome force of spring 136 in order to push lock prong 144 into transverse passage 138 and out of longitudinal passage 137 to facilitate assembly of button 82 with tubular member 108. Bushing 126 can be threaded onto threading 110 of tubular body 116 to lock bearing housing 124 into place.

When button 82 is released into a default position as determined by spring 136, lock prong 144 can be inserted into one of detents 114A (FIG. 10), 114B (FIG. 10), 114C and 114D in order to prevent bearing housing 124 from being rotated on bushing 126 about tubular element 108 and axis 80. As such, detents 114A, 114B, 114C and 114D can provide a plurality of discrete positions into which handles 72 and 74, through coupling with post 96, can be locked. Locking of bearing housing 124 via detents 114A-114D can additionally lock lower bearing 54B via coupling between linkages 62A and 64A and 62B and 64B, respectively.

Detents 114A-114D can be located at positions that facilitate reducing of a rod relative to a spinal column and that facilitate placement of handles 72 and 74 out of the way of reducing the rod at other levels of the spinal column. For example, detents 114A and 114C can be located along the axis of the rod, parallel to the spinal column, such as in a sagittal plane like plane 16 of FIG. 1. In such positions, notches 106 on rod-engaging feature 102 can be aligned with detents 114A and 114C. For example, detents 114B and 114D can be located transverse to the axis of the rod, transverse to the spinal column, such as in a transverse plane like plane 19 of FIG. 1. However, in other examples, a greater number or fewer detent positions can be provided, or can be located at different circumferential positions relative to axis 80.

Figure 14:
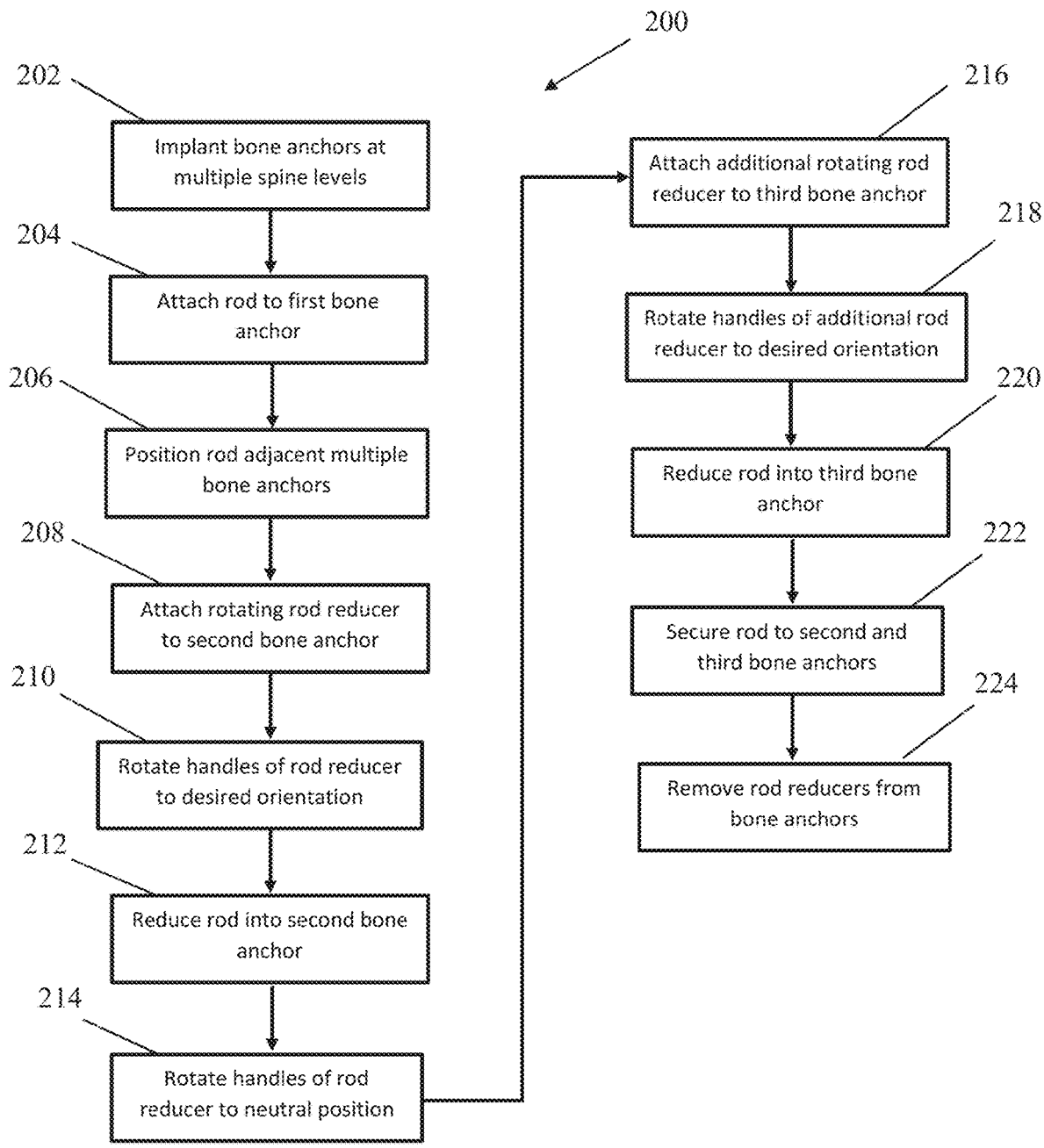
FIG. 14 is a line diagram illustrating steps of a method for reducing rods in a spinal procedure in accordance with the systems and methods described herein.

FIG. 14 is a line diagram illustrating steps of method 200 for reducing rods in a spinal procedure in accordance with the systems and methods described herein. Method 200 describes an exemplary method, but other methods with different, fewer or greater steps can be performed using the rotating rod reducers described herein.

At step 202, a plurality of bone anchors can be implanted onto a spinal column at multiple spine levels. For example, one of the medial and lateral side of the spine can be treated first, while the other can be treated subsequently. In other examples, both the medial and lateral side can be treated simultaneously. Bone anchors can be attached to multiple adjacent vertebrae in the spinal column. For example, the T7-T9 vertebra in the thoracic region of the spinal column can be contemporaneously implanted with bone anchors to treat scoliosis conditions.

At step 204, a rod can be attached to a first bone anchor. A rod can be situated in a housing of a first bone anchor attached to a fastener. The rod can be secured by attaching a closure element, such as a threaded fastener, to the housing. A rod reducer can be used to couple the rod to the second bone anchor. The rod reducer can be removed from the second bone anchor after the rod is secured to the second bone anchor housing. The rod reducer used in conjunction with the first bone anchor can be rotating if it is desired to be left in place, or can be non-rotating if it is to be removed.

At step 206, the rod can be positioned adjacent multiple bone anchors of the plurality of bone anchors. Step 206 can be conducted before the rod is secured to the first bone anchor. The rod can be positioned, such as above, openings in housings of second and third bone anchors. The second and third bone anchors can be adjacent the first bone anchor such that the first, second and third bone anchors are affixed to consecutive vertebrae, such as the T7-T9 vertebra.

At step 208, a first rotating rod reducer can be attached to the second bone anchor. A housing-engaging member of the first rotating rod reducer can be coupled to the second bone anchor while a rod-engaging member of the first rotating rod reducer can be positioned to contact the rod.

At step 210, handles of the first rod reducer can be rotated, or otherwise positioned, to a desired orientation. The handles of the first rod reducer can be rotated to actuate in a plane parallel with a sagittal plane of the spinal column. However, the handles can be rotated to any position that a surgeon, or another personnel, finds ergonomically suitable or that provides advantageous leverage for reducing the rod. A button of a locking mechanism can be actuated to rotate the handles to the desired position. The button can be released to permit the locking mechanism to prevent subsequent rotation of the handles. Other locking mechanisms not utilizing button can be used.

At step 212, the rod can be reduced into a second bone anchor, such as by actuating the handles. For example, the handles can be actuated from a first, open position to a second, closed position where the handles are closer together. Pulling of the handles closer together can draw the housing of the bone anchor up and around the rod using the housing-engaging member and the rod-engaging member.

At step 214, the handles of the first rod reducer can be rotated to a neutral position where the handles may not interfere with procedures being performed on other levels of the spinal column. For example, the handles of the first rod reducer can be rotated to be in a transverse plane of the spinal column, thereby clearing space above and below the vertebra to which the second bone anchor is attached. The handles of the first rod reducer can be rotated to other neutral positions not in the sagittal plane of the spinal column to facilitate or enhance the ability to attach an additional rotating rod reducer to a bone anchor attached to a vertebra immediately adjacent the vertebra to which the second bone anchor is attached.

At step 216, the additional rotating rod reducer can be attached to third third bone anchor that is attached to the vertebra immediately adjacent the vertebra to which the second bone anchor is attached. The handles of the first rotating rod reducer can be positioned to not interfere with operation of the additional rotating rod reducer because the handles can be adjusted to be in a neutral position. In other examples, a non-rotating rod reducer can be used to reduce the third bone anchor.

At step 218, handles of the additional rod reducer can be rotated to a desired orientation to perform reducing of the third bone anchor. For example, the handles can be rotated into an ergonomic position for the surgeon or a position where the surgeon can gain leverage. The handles can be locked into position with a locking device to perform reduction.

At step 220, the rod can be reduced into the third bone anchor using the additional rod reducer. For example, the handles of the additional rod reducer can be actuated from a first, open position to a second, closed position where the handles are closer together. Pulling of the handles closer together can draw the housing of the bone anchor up and around the rod using a housing-engaging member and a rod-engaging member.

At step 222, the rod can be secured to second and third bone anchors. The first rotating rod reducer and the additional rotating rod reducer can be removed from the second bone anchor and the third bone anchor so that closure members can be used to secure the rod to housings of the bone anchors. For example, a threaded fastener attached to a tip of a driver can be inserted through the housing-engaging member and the rod-engaging member to contact the housings of the second and third bone anchors.

At step 224, the first rotating rod reducer and the additional rotating rod reducer can be removed from the second and third bone anchors. Additional reduction of the rod at other levels or on an opposite side of the spinal column can subsequently be performed if advantageous.

The systems, devices and methods discussed in the present application can be useful in coupling one or more elongate stabilization members, such as rigid rods, to a plurality of bone anchors. In particular, the rotating rod reducers and methods described herein facilitate safe, effective and efficient reduction of bone anchors in spinal procedures. The rotating rod reducers can facilitate ergonomic and mechanically advantageous reduction of individual bone anchors with a rod. Additionally, multiple rotating rod reducers can be used to facilitate simultaneous reduction of close-by or adjacent vertebrae in the spinal column. Such benefits can improve patient safety by reducing over-application of force to rod reducers at individual vertebral levels as can result from awkwardly positioned reducer handles, and by reducing over-application of force to multiple vertebral levels by spreading the reduction force to multiple vertebrae. Such benefits can also reduce the time needed to perform surgical procedures, thereby reducing cost of the procedure and discomfort to the patent.

VARIOUS NOTES & EXAMPLES

Example 1 can include or use subject matter such as a rod reducer that can comprise a first elongate member, a second elongate member configured to slide along the first elongate member, a first bearing component rotatably connected to the first elongate member, a second bearing component rotatably connected to the second elongate member, a hinge mechanism comprising a first pair of linkages pivotably coupled to the first bearing component, a second pair of linkages pivotably coupled to the second bearing component, first and second rotation elements connecting the first pair of linkages and the second pair of linkages and first and second lever arms extending from the second pair of linkages, and first and second handles connected to the first and second lever arms, respectively, configured to cause the second pair of linkages to draw the first bearing component and the first elongate member toward the second bearing component, wherein the first bearing component and the second bearing component permit the hinge mechanism to rotate about the first and second elongate members.

Example 2 can include, or can optionally be combined with the subject matter of Example 1, to optionally include first and second bearing components that facilitate rotation about a common axis.

Example 3 can include, or can optionally be combined with the subject matter of one or any combination of Examples 1 or 2 to optionally include first and second handles that can rotate three-hundred-sixty-degrees about the first and second elongate members.

Example 4 can include, or can optionally be combined with the subject matter of one or any combination of Examples 1 through 3 to optionally include a locking mechanism configured to prevent rotation of the first and second handles about the first and second elongate members.

Example 5 can include, or can optionally be combined with the subject matter of one or any combination of Examples 1 through 4 to optionally include a locking mechanism that is configured to arrest rotation of the first and second handles about the first and second elongate members at a plurality of discrete positions.

Example 6 can include, or can optionally be combined with the subject matter of one or any combination of Examples 1 through 5 to optionally include a locking mechanism located on one of the first and second bearing components.

Example 7 can include, or can optionally be combined with the subject matter of one or any combination of Examples 1 through 6 to optionally include a locking mechanism comprising a biased button located on the second bearing component.

Example 8 can include, or can optionally be combined with the subject matter of one or any combination of Examples 1 through 7 to optionally include a locking mechanism comprising one or more detents located in an exterior surface of one of the first and second elongate members, a housing comprising a first longitudinal passage configured to receive the one of the first and second elongate members and a transverse passage configured to intersect the first longitudinal passage, a button configured to fit within the transverse passage comprising a second longitudinal passage and a projection member configured to extend into the second longitudinal passage, and a spring located between the button and the housing, wherein the spring is configured to bias the button into a first position where the projection member can be positioned within the first longitudinal passage to engage the one or more detents, and wherein the button can be actuated to push the button into a second position where the projection member can be positioned outside of the first longitudinal passage.

Example 9 can include, or can optionally be combined with the subject matter of one or any combination of Examples 1 through 8 to optionally include first and second bearing components each comprises a bushing.

Example 10 can include or use subject matter such as a rod reducer that can comprise a reducing mechanism comprising a first elongate member extending along an axis and configured to engage a bone anchor and a second elongate member configured to slide along the first elongate member along the axis and configured to engage a rod, a hinge mechanism slidably coupling the first elongate member and the second elongate member such that the first elongate member can translate relative to the second elongate member, a handle mechanism comprising a pair of handles coupled to the hinge mechanism and configured to cause the first and second elongate members to translate relative to each other and a bearing mechanism configured to permit the handle mechanism to rotate about the axis independent of the first and second elongate members.

Example 11 can include, or can optionally be combined with the subject matter of Example 10, to optionally include a bearing mechanism comprising a first bushing connected to the first elongate member and a second bushing connected to the second elongate member.

Example 12 can include, or can optionally be combined with the subject matter of one or any combination of Examples 10 or 11 to optionally include a bearing mechanism further comprising a first bushing housing configured to couple the first bearing to the handle mechanism and a second bushing housing configured to couple the second bushing to the hinge mechanism.

Example 13 can include, or can optionally be combined with the subject matter of one or any combination of Examples 10 through 12 to optionally include a locking mechanism configured to immobilize rotation of the handle mechanism relative to the reducing mechanism.

Example 14 can include, or can optionally be combined with the subject matter of one or any combination of Examples 10 through 13 to optionally include a locking mechanism including a button configured to toggle between a default immobilized state and an actuated free state.

Example 15 can include, or can optionally be combined with the subject matter of one or any combination of Examples 10 through 14 to optionally include a hinge mechanism comprising a first pair of linkages pivotably coupled to the first bearing component, and a second pair of linkages pivotably coupled to the second bearing component, the second pair of linkages including a pair of lever arms configured to couple to the pair of handles of the handle mechanism at a pair of cams extending from the pair of handles.

Example 16 can include or use subject matter such as a method of reducing multiple levels of a spinal column in a surgical procedure to correct a spinal deformity that can comprise implanting a first bone anchor to a first vertebra, the first bone anchor including a first housing having a first opening to receive a rod, implanting a second bone anchor to a second vertebra, the second bone anchor including a second housing having a second opening to receive the rod, implanting a third bone anchor to a third vertebra, the third bone anchor including a third housing having a third opening to receive the rod, positioning the rod in the first opening, securing the rod to the first housing, positioning the rod proximate the second opening and the third opening, coupling a first rotating rod reducer to the second housing, the first rotating rod reducer comprising first and second reducing elements that are configured to slide relative to each other and a first pair of a handles configured to slide the first and second reducing elements relative to each other when actuated, wherein the first pair of handles are configured to rotate about an axis of the first and second reducing elements, reducing the rod into the second housing using the first rotating rod reducer, rotating the first pair of handles into a transverse plane of the spinal column, reducing the rod into the third housing using an additional rod reducer and securing the rod to the second and third housings.

Example 17 can include, or can optionally be combined with the subject matter of Example 16, to optionally include first, second and third vertebrae that are adjacent to each other on a single side of the spinal column.

Example 18 can include, or can optionally be combined with the subject matter of one or any combination of Examples 16 or 17 to optionally include an additional rod reducer comprising a rotating rod reducer.

Example 19 can include, or can optionally be combined with the subject matter of one or any combination of Examples 16 through 18 to optionally include reducing the rod into the second housing using the first rotating rod reducer by rotating the first pair of handles into a sagittal plane of the spinal column.

Example 20 can include, or can optionally be combined with the subject matter of one or any combination of Examples 16 through 19 to optionally include reducing the rod into the second housing using the first rotating rod reducer by rotating the first pair of handles into an oblique position between a sagittal plane and a transvers plane of the spinal column.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more," In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at leak in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A rod reducer comprising:
a first elongate member;
a second elongate member configured to slide along the first elongate member;
a first bearing component rotatably connected to the first elongate member;
a second bearing component rotatably connected to the second elongate member;
a hinge mechanism comprising:
a first pair of linkages pivotably coupled to the first bearing component;
a second pair of linkages pivotably coupled to the second bearing component;
first and second rotation elements connecting the first pair of linkages and the second pair of linkages; and first and second lever arms extending from the second pair of linkages; and first and second handles connected to the first and second lever arms, respectively, and configured to cause the second pair of linkages to draw the first bearing component and the first elongate member toward the second bearing component;

wherein the first bearing component and the second bearing component permit the hinge mechanism to rotate about the first and second elongate members; and wherein the first and second bearing components facilitate rotation about a common axis.

2. The rod reducer of claim 1, wherein first and second handles can rotate three-hundred-sixty-degrees about the first and second elongate members.

3. The rod reducer of claim 1, further comprising a locking mechanism configured to prevent rotation of the first and second handles about the first and second elongate members.

4. The rod reducer of claim 3, wherein the locking mechanism is configured to arrest rotation of the first and second handles about the first and second elongate members at a plurality of discrete positions.

5. The rod reducer of claim 3, wherein the locking mechanism is located on the second bearing component.

6. The rod reducer of claim 3, wherein the locking mechanism comprises a biased button located on the second bearing component.

7. The rod reducer of claim 3, wherein the locking mechanism comprises:
   one or more detents located in an exterior surface of the second elongate member;
   a housing comprising:
      a first longitudinal passage configured to receive the second elongate member; and
      a transverse passage configured to intersect the first longitudinal passage;
   a button configured to fit within the transverse passage, the button comprising:
      a second longitudinal passage; and
      a projection member configured to extend into the second longitudinal passage; and
   a spring located between the button and the housing;
   wherein the spring is configured to bias the button into a first position where the projection member can be positioned within the first longitudinal passage to engage the one or more detents; and
   wherein the button can be actuated to push the button into a second position where the projection member can be positioned outside of the first longitudinal passage.

8. The rod reducer of claim 1, wherein the first and second beating components each comprises a bushing.

9. A rod reducer comprising:
   a reducing mechanism comprising:
      a first elongate member extending along an axis and configured to engage a bone anchor; and
      a second elongate member configured to slide along the first elongate member along the axis and configured to engage a rod;
   a hinge mechanism slidably coupling the first elongate member and the second elongate member such that the first elongate member is translatable relative to the second elongate member;
   a handle mechanism comprising a pair of handles pivotably coupled to the hinge mechanism and configured to cause the first and second elongate members to translate relative to each other; and
   a bearing mechanism configured to permit the handle mechanism to rotate freely about the axis independent of the first and second elongate members.

10. The rod reducer of claim 9, wherein the bearing mechanism comprises:
   a first bushing connected to the first elongate member; and
   a second bushing connected to the second elongate member.

11. The rod reducer of claim 10, wherein the bearing mechanism further comprises:
   a first bushing housing configured to couple the first bearing to the handle mechanism; and
   a second bushing housing configured to couple the second bushing to the hinge mechanism.

12. The rod reducer of claim 10, therein the hinge mechanism comprises:
   a first pair of linkages pivotably coupled to the first bushing; and
   a second pair of linkages pivotably coupled to the second bushing, the second pair of linkages including a pair of lever arms configured to pivotably couple to the pair of handles of the handle mechanism at a pair of cams extending from the pair of handles.

13. The rod reducer of claim 12, wherein each of the pair of lever arms is pivotably coupled to one of the cams of the pair of cams and not connected to the other cam of the pair of cams.

14. The rod reducer of claim 9, further comprising a locking mechanism configured to immobilize rotation of the handle mechanism relative to the reducing mechanism.

15. The rod reducer of claim 14, wherein the locking mechanism includes a button configured to toggle between a default immobilized state and an actuated free state.

16. The rod reducer of claim 9, wherein the bearing mechanism is configured to permit the handle mechanism to rotate freely about the axis three-hundred-sixty degrees.

17. A rod reducer comprising:
   a reducing mechanism comprising:
      a first elongate member extending along an axis and configured to engage a bone anchor; and
      a second elongate member configured to slide along the first elongate member along the axis and configured to engage a rod;
   a hinge mechanism slidably coupling the first elongate member and the second elongate member such that the first elongate member is translatable relative to the second elongate member;
   a handle mechanism comprising a pair of handles coupled to the hinge mechanism and configured to cause the first and second elongate members to translate relative to each other;
   a bearing mechanism configured to permit the handle mechanism to rotate about the axis independent of the first and second elongate members; and
   a locking mechanism configured to immobilize rotation of the handle mechanism relative to the reducing mechanism;
   wherein the locking mechanism includes a button configured to toggle between a default immobilized state and an actuated free state.

* * * * *

UNITED STATES PATENT AND TRADEMARK OFFICE
CERTIFICATE OF CORRECTION

PATENT NO. : 11,311,321 B2
APPLICATION NO. : 16/588610
DATED : April 26, 2022
INVENTOR(S) : Mast et al.

It is certified that error appears in the above-identified patent and that said Letters Patent is hereby corrected as shown below:

On the Title Page

Item (57), Line 12, please delete "beating" and insert --bearing-- therein.

In the Claims

At Column 15, Line 52, delete "beating" and insert --bearing-- therein.

At Column 16, Line 17, delete "therein" and insert --wherein-- therein.

Signed and Sealed this
Second Day of August, 2022

Katherine Kelly Vidal
*Director of the United States Patent and Trademark Office*